US011293002B2

(12) United States Patent
Zenhausern et al.

(10) Patent No.: US 11,293,002 B2
(45) Date of Patent: Apr. 5, 2022

(54) CELL CULTURE APPARATUS AND CULTURE METHODS USING SAME

(71) Applicants: UNIVERSITE DU LUXEMBOURG, Luxembourg (LU); ARIZONA BOARD OF REGENTS ON BEHALF OF UNIVERSITY OF ARIZONA, Tuscson, AZ (US)

(72) Inventors: Frederic Zenhausern, Fountain Hills, AZ (US); Paul Wilmes, Bettembourg (LU); Pranjul Shah, Esch-sur-Alzette (LU)

( * ) Notice: Subject to any disclaimer, the term of this patent is extended or adjusted under 35 U.S.C. 154(b) by 807 days.

(21) Appl. No.: 15/576,590

(22) PCT Filed: May 27, 2016

(86) PCT No.: PCT/EP2016/062024
§ 371 (c)(1),
(2) Date: Nov. 22, 2017

(87) PCT Pub. No.: WO2016/189142
PCT Pub. Date: Dec. 1, 2016

(65) Prior Publication Data
US 2018/0155665 A1 Jun. 7, 2018

Related U.S. Application Data

(60) Provisional application No. 62/166,940, filed on May 27, 2015.

(30) Foreign Application Priority Data

Jun. 24, 2015 (LU) .......................................... 92752

(51) Int. Cl.
C12M 3/06 (2006.01)
C12M 1/00 (2006.01)
(Continued)

(52) U.S. Cl.
CPC .............. *C12M 23/16* (2013.01); *C12M 3/04* (2013.01); *C12M 3/065* (2013.01); *C12M 21/08* (2013.01);
(Continued)

(58) Field of Classification Search
CPC ........ C12M 23/16; C12M 3/04; C12M 3/065; C12M 21/08; C12M 23/06; C12M 29/04; C12M 29/12; C12M 35/08
See application file for complete search history.

(56) References Cited

U.S. PATENT DOCUMENTS

| 2001/0019704 A1* | 9/2001 | Gunter ................ B01L 3/50851 422/534 |
| 2012/0009671 A1* | 1/2012 | Hansen .................. C12M 23/16 435/325 |
| 2015/0072413 A1* | 3/2015 | Zenhausern ........... C12M 35/08 435/347 |

FOREIGN PATENT DOCUMENTS

| WO | WO-2007/064635 A1 | 6/2007 |
| WO | WO-2013/144253 A1 | 10/2013 |

OTHER PUBLICATIONS

Kim, H.J., et al., "Human gut-on-a-chip inhabited by microbial flora that experiences intestinal peristalsis-like motions and flow", Lab Chip, 2012, 12:2165-2174.
(Continued)

*Primary Examiner* — William H. Beisner
*Assistant Examiner* — Danielle B Henkel
(74) *Attorney, Agent, or Firm* — Foley & Lardner LLP

(57) ABSTRACT

Cell culture apparatus for emulating gastrointestinal tract conditions and comprising at least two adjacent, microfluidic, cell cultivation channels separated by a permeable or semipermeable membrane, a first channel carrying gastrointestinal tract epithelial cells or tissues and a second channel carrying luminal and preferably mucosal microbiota, and
(Continued)

wherein said second channel comprises one or more dwell chambers capable of providing a location for unattached luminal flora to reside away from any direct flow in said second channel, permits modelling of multiple sections of the gastrointestinal tract and control of retention times.

17 Claims, 5 Drawing Sheets

(51) Int. Cl.
  *C12M 1/42* (2006.01)
  *C12M 3/04* (2006.01)
  *C12M 3/00* (2006.01)
  *C12M 1/12* (2006.01)
(52) U.S. Cl.
  CPC ............ *C12M 23/06* (2013.01); *C12M 29/04* (2013.01); *C12M 29/12* (2013.01); *C12M 35/08* (2013.01)

(56) References Cited

OTHER PUBLICATIONS

International Search Report and Written Opinion in PCT/EP2016/062024, dated Aug. 18, 2016, 9 pages.

\* cited by examiner

Exploded view of the microGUT model

Characterisation of fluid retention times

Fluid retention times

CELL CULTURE APPARATUS AND CULTURE METHODS USING SAME

CROSS-REFERENCE TO RELATED APPLICATIONS

This application is a U.S. National Phase of International Patent Application No. PCT/EP2016/062024, filed May 27, 2016, which claims priority to U.S. Provisional Patent Application No. 62/166,940, filed May 27, 2015, and Luxembourg Patent App. No. 92752, filed Jun. 24, 2015, the entire disclosures of which are incorporated herein by reference.

The present invention relates to cell culture apparatus capable of emulating a part or parts of the gastrointestinal tract, methods for constructing same, and methods for using same.

Mixed microbial communities play pivotal roles in governing human health and disease (1, 2). Recent large-scale metagenomic sequencing efforts have corroborated the notion that humans should be considered as super-organisms, and that imbalances in microbial community structure and function (dysbiosis), particularly in the gastrointestinal tract, can lead to disease (1, 2).

Although large-scale "meta-omic" studies are significantly advancing knowledge of the human microbiome, none of the present study types, including cross-sectional, case-control and longitudinal, have the necessary statistical power to allow causation to be inferred from patterns of association between variables, due to their nascent complexity and heterogeneity (3).

Furthermore, little is clear about the mechanisms behind dysbiosis, and most studies have mainly taken case-control, comparative approaches to analyse and establish which species have exhibited altered abundance during disease. The flaw in this approach is the lack of understanding of whether the change in abundance was causative of the disease pathogenesis, or a mere response to the altered physiological homeostasis.

Thus, there exists a need for an in vitro model of the gastrointestinal tract which will allow exploration of hypotheses related to human-microbe interactions, and testing of the pathogenesis of diseases related to the gut.

WO2013144253 discloses a microfluidics-based co-culture device allowing partitioned but proximal co-culture of human and microbial cells while simultaneously allowing molecular interactions between the two cultures across a semi-permeable membrane. This system provides a tool to investigate the role of human microbiome interactions in the pathogenesis of idiopathic diseases hypothesized to have roots in a dysbiotic gut. Compatibility with high-resolution omic analyses enables a molecular level snapshot of host-microbe interactions. The system disclosed in WO2013144253 is modular, and it is possible to link up several modules to attempt to mimic the proximal colon, for example. However, the means for doing this are complex, making it difficult to run multiple devices, either in series or in parallel.

In addition, transit time in the gut is an important factor in determining host-microbe interactions, and is something that cannot be modelled in such a system. Bowel transit time is highly variable within individuals, as well as across the population. A number of factors, including age, health status, and diet, is linked to the changes in the bowel transit time. The bowel transit time has a substantial role to play in regulating host-microbe interactions and vice versa (4-6).

Thus, in a first aspect, the present invention provides a cell culture apparatus for emulating gastrointestinal tract conditions and comprising at least two adjacent cell cultivation channels separated by a permeable or semipermeable membrane, wherein at least two of said channels each has a cross section for the majority of the length of said channel having two dimensions, and wherein at least one dimension of each of said cross sections does not exceed 1000 µm, each said channel being provided with entrance and exit means to permit the passage of media through at least a portion of the channel having a cross sectional area of no more than 10 mm$^2$, a first channel of said at least two channels being adaptable to support growth of gastrointestinal tract epithelial cells and a second channel of said at least two channels being adaptable to support luminal, and preferably also mucosal, microbiota, and wherein said second channel comprises one or more dwell chambers capable of providing a location for unattached luminal flora to reside away from any direct flow in said second channel.

It is an advantage that apparatus of the present invention, also referred to herein as microGUT, permits, in various embodiments:

(i) Co-culture of human epithelial cells with sampled human gastrointestinal microbiota;

(ii) Inclusion of representative gastrointestinal microbiota (mucosal as well as luminal microbiota);

(iii) Mimic the residence times of the various sections of the human gastrointestinal tract via an automated programmable platform;

(iv) Continual monitoring of the physicochemical parameters (pH, oxygen concentration, metabolic crosstalk, etc.);

(v) The possibility to acquire time-resolved samples from the various model sections of the gut; and (vi) Independent access to individual contingents, following targeted perturbations to elucidate the effects of co-culture on the host and microbial contingents using dedicated high-resolution high-throughput molecular omic analyses.

Apparatus of the present invention may be used for co-culture of any two or more types of cells, typically with one sedentary community, such as human cells/tissue(s) and one more transient, such as microorganisms, with which the first set may come into contact under in vivo conditions. Typically, this might be gut tissue, for example human organoids, and luminal and/or mucosal microbiota.

The apparatus, also referred to herein as microGUT, is capable of emulating gastrointestinal tract conditions, in that cells, tissues, fluids and other components may be introduced into the apparatus to provide the relevant parts of the gut environment such as to enable study of microbiota/gastrointestinal tissue interactions in two or more parts of the gut.

The parts of the gut that may be emulated include those after the stomach, such as the jejunum, duodenum, small intestine and proximal colon, including the ascending, transverse and descending colons. More preferably, the small intestine and the proximal colon are emulated, as the gut microbiota are more prevalent in these areas, and have been associated with a number of conditions affecting human health.

In order to emulate gut conditions, it is preferable to provide cells typical of that area of the gut, and in similar proportions, together with an appropriate nutrient stream. Typically, the channels are of such a size as to be able to provide microfluidic properties, with one dimension of the channels, in cross-section, not exceeding 1 mm, for the majority of their length. Given that the gut is typically very long, it is appropriate that the channels are also long enough to provide a suitable emulation. However, given laboratory and manufacturing constraints, this length is typically no more than a metre for each section of the gut, and is suitably coiled such as to reduce the overall length of the apparatus.

For those channels incorporating gut tissue, there is generally no requirement to separate the individual communities in the different sections of the gastrointestinal tract, although it is generally preferable to seed each area with appropriate cells and in appropriate ratios. It is generally preferred to apply selected nutrients to the various gut areas, and so a gasket, or other block, is suitably placed at locations effective to substantially isolate nutrient feeds. Points of access can then be provided to the passage of nutrients, which access the gut tissue channel, suitably via a permeable or semipermeable membrane.

It is preferred to provide blocks in the microbiota channel, at or proximal to, the dwell chambers, in order that the non-adherent luminal microbiota are required to travel through the dwell chamber, or in close proximity to the mouth of the chamber, such that there is a significant likelihood that the micro-organisms will enter the chamber, where they will remain for a period. Said period is typically determined by any agitation present in the chamber, as well as the size and form of the chamber, as discussed below.

One advantage of the invention is that it is possible to provide a microfluidic model of the human gastrointestinal tract allowing co-culture of sampled faecal inoculates with human intestinal cells, and that overcomes the limitations and complexities of the existing in vitro models of the human gastrointestinal tract (3, 4). Apparatus of the invention can provide a microfluidics-based dynamic human gut model encompassing modules for the small intestine, the ascending colon, the transverse colon and the descending colon. It is possible to model the dynamics of some or all of the human gut, such as optimisation of retention times, mucosal dynamics, pH gradients, proper shear stresses, and oxic-anoxic gradients on a miniaturised platform.

The present invention provides dwell chambers, also referred to herein as reservoirs, for non-adherent luminal microbiota. Such microbiota may comprise any non-adherent micro-organism located in the lumen. Most are bacteria, and will often be referred to herein as bacteria, but it will be appreciated that the term includes all non-adherent luminal microbiota. Given that such bacteria are non-adherent, then it will be appreciated that continuous stirring of the bioreactor is advantageous to stimulate and support their growth.

In a preferred embodiment, the dwell chambers are equipped with agitating means. Suitable agitating means may take any suitable form, including pumps located in a duct with inlet and outlet communicating directly with the chamber, rotatory fins, either as a fan arrangement or located in tracks, for example, about the inner circumference of the chamber wall, or impellers mounted on suitable axles. More preferably, the agitation is provided by a stirring rod, and it has been found that a ferrometallic or magnetic flea, especially one suitable for autoclaving, serves the purpose well. When the terms flea or stirring rod are used herein, it will be understood that these terms are inclusive of any other suitable form of agitation means, unless otherwise apparent.

The flea in each well can be set for the same or a different speed, and it has been found that this can substantially affect the residence time of the non-adherent microbiota, as well as affect diffusion of nutrients and metabolites, for example. In developing the model, we used a controlled dilution-based strategy to program the retention times of the individual bioreactors, by controlling the mixing of the incoming fresh media to the bioreactor to control the dilution rate of the bioreactor contents. Faster mixing rates lower retention times, as the entire contents of the dwell chamber, also referred to as a bioreactor herein, will rapidly be flushed out. Likewise, slower mixing rates lead to longer retention times, as the contents of the bioreactor will need a much longer dilution process.

Preferred volumes of the dwell chambers are between 0.5 ml and 50 ml, and preferably between 2 and 50 ml, inclusive, although it will be understood that the size of the dwell chamber for any given model will be determined by the person skilled in the art. Thus, depending on the size of the model and what is desired to achieve, the dwell chambers can vary from about 0.5 ml up to ~1l, although the more preferred range is as above.

It will be understood that the dwell chamber for each stage of the gut model may vary according to the dwell time to be achieved, and in one model, the initial dwell chamber is ~10 ml, immediately prior to the small intestine, stepping up to 20 ml prior to the ascending colon, then 30 ml prior to the transverse colon, and finally 40 ml prior to the descending colon.

It will also be appreciated that, in accordance with the foregoing disclosure, the flea, where present, affects retention, or dwell, times, and the speed of each stirring rod can be selected to moderate the dwell time in each chamber. This is advantageous for fine tuning dwell times, or altering dwell times to mimic conditions in the gut, such as diurnal activity rhythms.

For ease of manufacture, dwell chambers will generally be of a regular shape. A bowl shape is not generally preferred as dwell times are substantially reduced in such a configuration. More preferred is cylindrical hollow with a flat bottom, over which a flea can be located. A motor, preferably programmable and variable speed, can be located in proximity to the bottom of the well in order to drive, or actuate, the flea. In addition, well shapes can include angles, although such will generally lead to an accumulation of adherent microbiota, so will generally only be preferable if this is what it is desired to achieve. A flask shaped well, with a narrower neck, can also lead to substantially increased retention, but this can also lead to difficulties in circulating all of the microbiota in the luminal cavity. In general, it will be appreciated that all dwell chamber shapes may be modified as to their dimensions, particularly concerning ratio of depth versus cross-sectional area, so as to reflect different needs e.g. for the microbial growth conditions regarding distance from the flowing culture media.

It will further be appreciated that the dwell chambers can be made of any suitable material but that, in general, it is preferred to form the chambers from the same material that forms the lower wall of the apparatus bounding the luminal channel.

In order to avoid any unnecessary exceptions to the in vivo conditions being modelled, it is preferred to implement a straightforward flow-in-flow-out strategy analogous to the human gastrointestinal tract. The present invention envisages flow-splitting methodology, but this is generally not as preferred, as it may result in different microbial niches and communities in parallel channels, which may lead to artificial effects.

Preferred retention times, in one embodiment, accord with the industry standard SHIME model (7).

In one embodiment, faecal communities may be used as the test cultures for the luminal channel. These may be introduced directly and cultured, or the pooled faecal community can be cultured externally in a bioreactor setup for 3-6 weeks to allow stabilisation of the community before inoculation. In general, it is preferred to allow the inoculated apparatus to equilibrate before starting to introduce test regimens and/or starting to take readings, other than for calibration and control purposes.

In one embodiment, it is preferred to characterise the stabilised community using metagenomic sequencing to ensure that the community profile is representative of the gastrointestinal microbiota.

In another embodiment, it is preferred to co-culture complex faecal communities with human epithelial cells and/or tissues along the entire apparatus. It is preferred to vary the composition of the human cells along the length of the simulated gut to create a representative epithelial barrier in the apparatus. Higher ratios of absorptive cells in the small intestine and higher ratios of goblets (mucus-producing) cells in the descending colon section are generally preferred.

Apparatus of the present invention may be used, for example, to study such subjects as; nutrition, metabolism and host-microbial interactions, the effect of commercially available pre- and/or probiotics on the microbiota, and other subjects that will be apparent to those skilled in the art. Related effects of the human epithelial cells can be characterised via multi-omic analyses. Other tests include testing the efficacy of pre-, pro- and synbiotics to modulate the human gastrointestinal microbiota, and to assay health benefits or support of therapeutic interventions in patients.

The culture apparatus of the invention may be made of any suitable material or materials, such as biocompatible glass or plastic. Composite and multilayer materials may be used, such as to provide structural integrity but with surfaces suited to cellular adhesion, or the whole may be made of a suitable, biocompatible, rigid plastic, preferably one that is not toxic, or not substantially toxic to the cells being cultured. A preferred plastics material is polycarbonate, or polystyrene that has typically been made wettable by oxidation.

The channels may be provided by any suitable means, including targeted laser evaporation or guided, heated boring apparatus, but the provision of a membrane between channels established in this manner can prove difficult, although this can be achieved by leaving a thin wall between the two channels.

More preferred is to construct the apparatus in layers and to sandwich a suitable membrane between respective channels. For example, two channel-containing layers may be provided, each having a channel provided in one surface, a groove in the surface defining three sides of the channel, or as many sides as desired, but leaving one side open. When the channel-containing sides of the layers are brought together, they can be brought together such that the channels are in register. A membrane-containing layer may be located between the two channel-containing layers, thereby to locate a membrane between the two channels, the membrane defining the final side of each channel. It will be appreciated that this process may be suitably modified to accommodate multiple, adjacent channels. A particularly preferred embodiment of the present invention has a nutrient channel for the gut tissue, said channel typically being of similar dimensions to the other two, and being separated from the gut tissue channel by means of a permeable or semipermeable membrane. The gut tissue channel, for example, will have open sides that can be completed by matching to each of the luminal microbiota channel and the nutrient channel, and sandwiching a membrane-containing layer therebetween. A layer containing a channel that is flanked by two other channels may typically be a layer that has the thickness of the channel it defines and wherein the channel is a slot cut in the layer. It is generally preferred that all channels of the apparatus are effectively constructed in such a manner, with the layer from which they are cut acting as a gasket between membrane layers.

The thickness of the layers may be uniform or contain protrusions and/or recesses such as may be used to assist in engaging the other layers with which they are intended to interact. There is no limit to the shapes that may be used, and it is possible that a protrusion may pass completely through a hole in a middle layer to engage with a hole in a third layer, for example.

The membrane-containing layer may consist entirely of membrane material provided as a membrane, and is preferably suitably tensioned until secured between the channel-containing layers, or may comprise a suitable web, matrix or lattice supporting the membrane prior to sandwiching. Such web, lattice or matrix may be removed after the membrane has been sandwiched, but it is generally preferable to leave it as part of the apparatus.

The membrane may be secured to either or both of the channel containing layers with which it interacts by any suitable means. Clamping may be used, but it is preferred to use an adhesive, or to cause the membrane to adhere to the channel containing layers. The latter may be effected by sonication when one or both of the membrane layer and channel containing layer are formed from compatible materials. Suitable adhesives for plastics are well known in the art, but are less preferred owing to the accuracy required for the small parts used. A particularly preferred method of adhesion is thermo-adhesion, whereby the construct is heated by irradiation, or in an oven, to cause at least one plastics material in the apparatus to become sufficiently tacky to adhere to an abutting layer.

The membrane may be permeable or semipermeable as required by the skilled person. It is preferred that the membrane does not permit passage of cells from one channel into another channel, otherwise the membrane may be selected such as to permit all molecules to freely pass between channels, or to more selectively permit passage. This may be achieved by providing suitably selected pores, such as ionic filters, hydrophobic, hydrophilic, or size filters. Semipermeable membranes are those which provide selective permeability for other than size of the molecules that can pass across the membrane. Semipermeable membranes are preferred.

The channels separated by a membrane have a majority of their length with a cross sectional area of no more than 10 $mm^2$, and preferably no more than 1 $mm^2$. It is generally preferable that the depth of at least one channel is no more than 500 µm in that portion having a cross sectional area of no more than 10 $mm^2$, and preferably all channels generally have a cross sectional area of no more than 1 $mm^2$ for the majority of their lengths. This is to take advantage of microfluidics, which, without being bound by theory, allows the flow of fluids in restricted diameter channels, with laminar flow and reduced Reynold's number.

The channels, other than at the dwell chambers, preferably have a uniform cross section for their entire length, or substantially their entire length between entrance and exit means, in order to permit even flow of any media. The entrance means and exit means may simply be holes in the material defining the channels or chambers, or may comprise structures for affixing suitable pump means to. For example, the entrance and/or exit means may comprise a nipple onto which may fit a tube from a pump.

The channels may be provided in any configuration desired, such as straight or circular, for example. Straight channels may be employed where multiple experiments are desired to be carried out, and the sets of adjacent channels may be provided in side by side arrangement in an elongate panel, for example.

In one preferred embodiment, the channels take the form of a swirl, or paired helix, in a form that might be obtained by drawing in a length by rotating the centre, and as is illustrated in accompanying FIG. 1. This assists in maximising the length of the channels while using a minimum of space. In this configuration, it is preferred that the entrance and exit points are located at the outer ends of the swirl. The swirls are connected via at least the luminal cultivation channel, from which may depend a dwell chamber. Thus, when there are at least two swirls, a dwell chamber may be associated with that portion of the channel linking the two swirls. In the embodiment involving configuring the channels as swirls, the location of the dwell chambers may generally be dependent on their cross-sectional area as compared to the cross-section of the specific form of the channels, such as directly and concentrically under such formed channel, eccentrically positioned, or otherwise located as determined by the skilled person, including, as noted above, being positioned between consecutive swirls.

The entrance points, or means, may permit or comprise a plurality of media pumps, such as micropumps, or injection apparatus. These may be continuous, discontinuous, or peristaltic, and may be arranged such that, none, one, or more is active at any given time.

The nature of the media to be pumped through the channels is any that is deemed appropriate by one skilled in the art, and may be a liquid or a gas, or a gaseous liquid, and may comprise nutrients, markers, or any other substance that it is desired to pass through the channels or expose the contents of the channel to.

As used herein, the term "cell culture", and associated terms, refers to a culture of a microorganism, a single, preferably eukaryotic, cell type, or a cell community, such as a tissue, adhered, preferably as a monolayer or consortium, on one or more walls of a channel. In the luminal channel, non-adherent cell cultures are also present.

The cell culture or cultures are preferably established prior to conducting any experiments, and may be seeded and cultured prior to inoculating the apparatus, varying nutrient flow as desired while establishing a culture.

It will be appreciated that the molecular interactions permitted by the apparatus of the invention can be probed and analysed in any manner desired, such as by high-resolution molecular methods, including genomics, transcriptomics, proteomics, and metabolomics. In particular, the apparatus allows separation of the individual channels following, for example, an experiment, thereby allowing subsequent biomolecular extractions from the respective cell contingents. It will be appreciated that separation may be effected by cutting the layers apart, or by constructing the apparatus in such a way as to permit disassembly after use. This may be achieved by heating or sonicating the apparatus after use, where such was used to achieve initial bonding, and where it will not significantly adversely affect the results of the experiment, or may be achieved by using an adhesive that does not fully set, or simply by unclamping the apparatus, if a clamp is used, for example. Other means for taking the apparatus apart will be apparent to those skilled in the art.

In one embodiment, the whole or part of the apparatus may be immersed in liquid nitrogen following an experiment. The frozen constituents may then be subject to channel separation and biomolecular extractions on the cell populations present in the respective channels, for example.

Apart from ports for the introduction of medium into the apparatus, additional ports for specific experiments can also be included in the design. The dimensions of the channels can preferably be chosen to take advantage of the full surface area of the circular membrane and to provide ample surface area (approximately 840 $mm^2$ per channel) for the culture of appropriate cell numbers. Obtaining representative biomolecular fractions for downstream high-throughput omics typically requires $10^6$ human cells, which translates to a channel surface area of around 2400 $mm^2$, which in turn may require the stacking of up to three sets of apparatus on top of each other.

It is generally preferred that, prior to inoculation, the side of the semipermeable membrane exposed to the luminal microbiota is layered with mucus, for example, obtained from: the HT29-MTX human cell line (8, 9); resected human intestinal tissue (10); or with porcine mucin gel (11), to assist initial microbial adhesion. Mucus (mucin) may be further supplied to the microbial community throughout the period of incubation by inclusion in the growth medium or by secretion by HT29-MTX cells in the human cell channel and subsequent diffusion into the microbial cell channel. The pore size of mucus is typically large enough for it not to prevent diffusion of biomolecules (12). Consequently, efficient molecular exchange can be maintained across the whole membrane-mucus layer.

Fluidic movement can be activated using an external syringe pump for precise liquid delivery which in turn can be controlled using a digital controller programmed with the LabView software package (National Instruments, Austin, Tex., USA). The pumps preferably interface with the apparatus using a polyether ether ketone (PEEK)/silicone tubing connection to provide a tight and reliable seal (13), although the skilled person will be able to provide any suitable pump and connector. The apparatus and pump can be placed in an incubator and controlled by an external computer running an automated LabView script to direct media exchange (14). For a human proximal colon apparatus, a flow rate of 7.3 μh can be used to guarantee a medium exchange rate of 52 h. For other apparatus, flow rates can be adjusted according to apparatus designs and/or layouts. However, in all cases, it is generally preferred to maintain the flow rate sufficiently low to avoid excessive detachment of cells due to shear stress. Before any culture experiments are carried out, it is generally desirable to perform partition tests by introducing molecules and particles of specific sizes into the medium and measuring if they are transferred across the membrane.

In a preferred embodiment, representative human cell lines that are well established cellular models and that, in the human body would naturally be in contact with mixed microbial communities, are selected for inoculation of the apparatus' human cell compartment(s). Faecal inoculate can be obtained from healthy human volunteers. Following successful co-culture of the human cell lines in conjunction with the mixed microbial communities, cultivation involving sampled human cells/tissue and associated mixed microbial communities may also be undertaken. Such samples can be obtained either by direct sampling or during routine medical procedures, e.g. gastroscopy or colonoscopy.

In this embodiment, specialised media are preferably used for the culturing of both cell populations. Initially, it is preferable that only human epithelial cells (9:1 mixture of Caco-2 (15) and HT29-MTX (8) cells) are grown in the apparatus until a fully differentiated cell monolayer is formed. Cell lines can be obtained from the American Type Culture Collection (ATCC; Manassas, Va., USA). For human cell culture, Dulbecco's modified Eagle's medium (DMEM) can be flowed through both the nutrient channel and the luminal channel. Following the establishment of stable cell monolayers (as determined by optical microscopy; expected after approximately 2-3 weeks), a complex medium that represents terminal ileal chyme (16, 17) can be flowed through the microbial channel. Following equilibration, the microbial cell culture channels can be seeded with fresh faecal inoculate (11). Following the establishment of microbial communities (as determined by optical microscopy), the human cell culture medium can be modified to just include inorganic salts as buffering agents. The apparatus can then be operated until the establishment of a stable functional state (approximately 3 weeks (18)). The established microbial communities can be monitored by a combination of high-resolution molecular microbial community profiling and metabolomics to provide a base line for the apparatus setups and experimental conditioning.

Oxygen concentrations may be measured and modelled by microfluidic diffusion analysis (19). The DMEM and buffer solution can subsequently be adjusted by using a defined length of slightly gas permeable silicone tubing through which the solutions can be flowed prior to introduction into the human cell channel. Conversely, nitrogen gas can be bubbled through the microbial growth medium prior to introduction into the syringe and gas impermeable PEEK tubing can be used to establish complete anaerobic conditions. For example, it may be desirable to make the human cell culture channel from oxygen permeable polydimethylsiloxane (PDMS) instead of polycarbonate.

In the accompanying Figures, the spiral modules were designed using the AutoCAD software package (Autodesk, San Rafael, Calif., USA). The apparatus was created by bonding together separate spiral channels made of polycarbonate polymer. These channels were formed by computer numerically controlled (CNC) machining of 0.2 mm and 0.5 mm thick polycarbonate plate stock [Becker and Gartner, 2000]. The use of polycarbonate allows for accurate control of the respective levels of dissolved oxygen within the channels, such as aerobic conditions for gut tissue and anaerobic conditions in the luminal cell culture channel.

The channels have a wall thickness of 800 µm, selected to maximise structural integrity, although other thicknesses will be apparent to those skilled in the art. In the accompanying Figures, the channels are 200 µm deep and 4 mm wide. The length of each channel is typically between 0.2 m and 0.5 m, and fit into a circular area of a diameter of between 42 mm and 70 mm. The channels are partitioned by semipermeable polycarbonate membranes of similar size, and are nanoporous with a thickness of 6 µm; Advantec MFS Inc., Dublin, Calif., USA. The channels are bound to either side of the permeable membrane using fitted and biologically compatible double-sided pressure sensitive adhesive (Adhesives Research, Glen Rock, Pa., USA).

There is preferably provided a dedicated perfusion channel, separated by means of a semipermeable membrane, adjacent to the gut tissue cell culture channel, e.g. in which Caco-2 cells are cultured, which provides diffusion-dominant perfusion to the Caco-2 cells, thereby mimicking the in vivo perfusion dynamics, and allowing perfusion of the basolateral surface of the Caco-2 cells. There are significant advantages with this kind of perfusion mechanism (20).First, intestinal epithelial cells are normally perfused via diffusion in vivo, so that this mode of perfusion helps to recreate the extracellular matrix conditions for the cells. Secondly, it has already been shown using transwell membrane inserts that diffusion based perfusion to basolateral surface speeds up epithelial cell growth, differentiation, and polarisation, thereby reducing cell culture time from 21 days to 7 days (21), which is a significant improvement on assay time, and reduces other costs associated with reagents, for example. Finally, as the cells are perfused using dedicated perfusion channels, they are prevented from experiencing shear stress that may occur without a separate perfusion channel. This can be advantageous for cell types in which shear stress can change the gene expression profile of cells. In such cases, the membrane that borders the perfusion channel preferably has a mean pore size of between 0.5-2 µm. In general, membranes separating cell cultures, especially separate cultures of human and microbial cells, preferably have pore sizes in the nanometre range, such between 1 and 20 nm, preferably between 1 and 10 nm.

In general, it will be appreciated that dedicated perfusion channels do not need to have a cross section of 1 $mm^2$ or less, as microfluidics is of less concern for such channels.

In general, any polycarbonate layers used in the present invention may be designed with one or more glass viewing windows to facilitate easy optical inspection of the co-cultures.

For inoculation of the human cell channels, representative human cell lines that form monolayers may be chosen, e.g. the AGS (22), Kato III (23) or MKN28 (24) cell lines, for the stomach compartment, and the Caco-2 and HT29-MTX cell line mixtures for the subsequent compartments. Animal, mammal, or human cells derived from patient samples may also be used as inoculum, as may cells or artificial tissues, also known as organoids, derived from induced pluripotent stem cells (http://mbio.asm.org/content/5/4/e01438-14.full). In the human intestinal model, stable mono layers of cells can be allowed to form in the channels before microbial cell culture medium comprising SHIME feed and artificial pancreatic juice (18) are fed through the successively arranged microbial community channels. In order to provide a supply of sufficiently rich medium to the human cell lines, each channel may be supplied with fresh DMEM. Following equilibration of the system, fresh human faecal samples can be used as inoculate and the human cell culture medium rarefied. Following the establishment of a stable functional state within the respective mixed microbial communities (18), specific measurements can be carried out on the regions of interest.

In some preferred embodiments, in apparatus of the present invention, each dwell chamber is used to demarcate an emulated section of gut.

In another embodiment, apparatus of the present invention further comprises one or more biosensors. Said biosensors may be for monitoring the quality and/or state of the system, and optionally comprise an optical biosensor and/or an electrochemical biosensor.

There is further provided a method for using the apparatus of the present invention, comprising populating said first channel with gut tissue, including organoid tissue, preferably selected from cells making up the gut wall in the small intestine and/or colon, and passing microbiota into said second channel and investigating an interaction between the populations of said channels.

In a further method, the semipermeable membrane separating the said two channels is lined with mucin prior to inoculation.

There is further provided a method of making apparatus of the present invention, comprising cutting one or more channels from a gasket layer and sandwiching a suitable membrane between layers defining adjacent channels.

Figure 1:
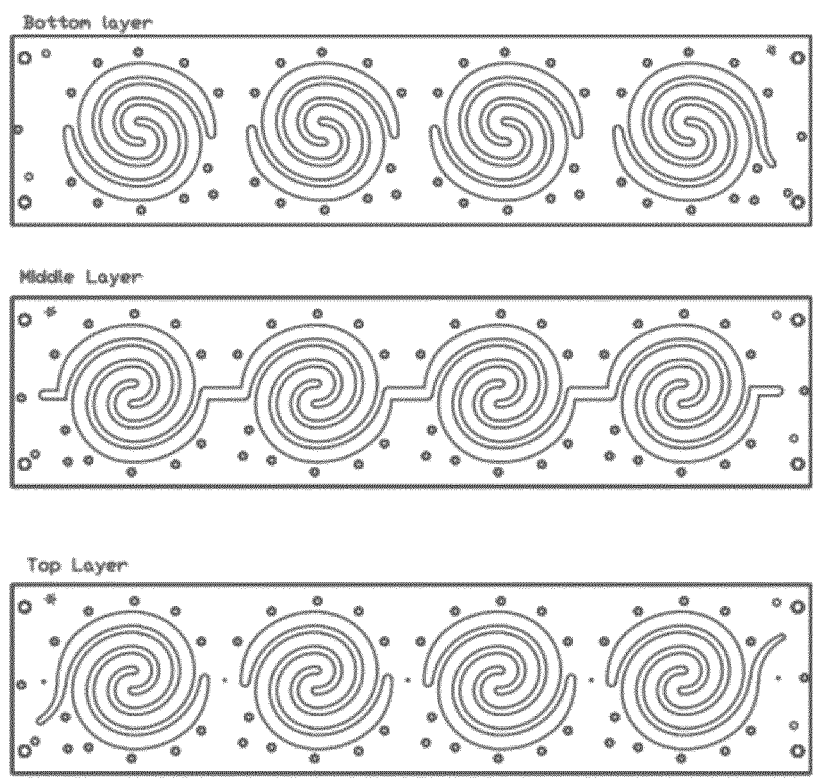
FIG. 1 shows cut-out gaskets for use in the invention.

In FIG. 1, the gaskets discussed above are shown with cut-outs corresponding to the channels of the apparatus of the invention. It will be noted that the top and bottom channels are non-continuous. This enables the nutrient channel to provide different nutrients and/or different flows of nutrient according to the section of gut to be emulated, while the bottom channel thereby forces any non-adherent cells to pass through the dwell chambers located in proximity to the barriers between the modules.

Figure 2:
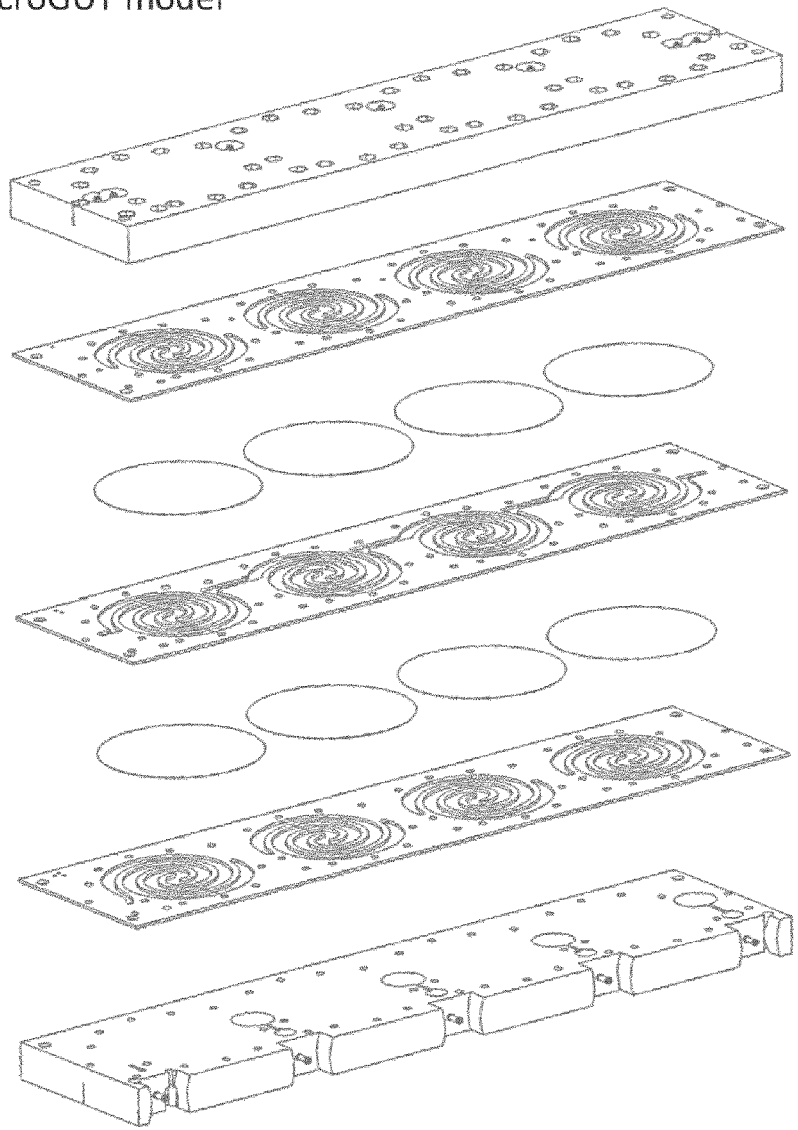
FIG. 2 shows an exploded view of apparatus of the invention.

In FIG. 2, there is shown an exploded view of the apparatus of the invention, showing the discs of semipermeable membrane located between the cut out gaskets. The top and bottom are typically formed from plastic, such as polycarbonate, in which are provided assorted access points for measurements, nutrient charging and cell inoculation, for example.

Figure 3:
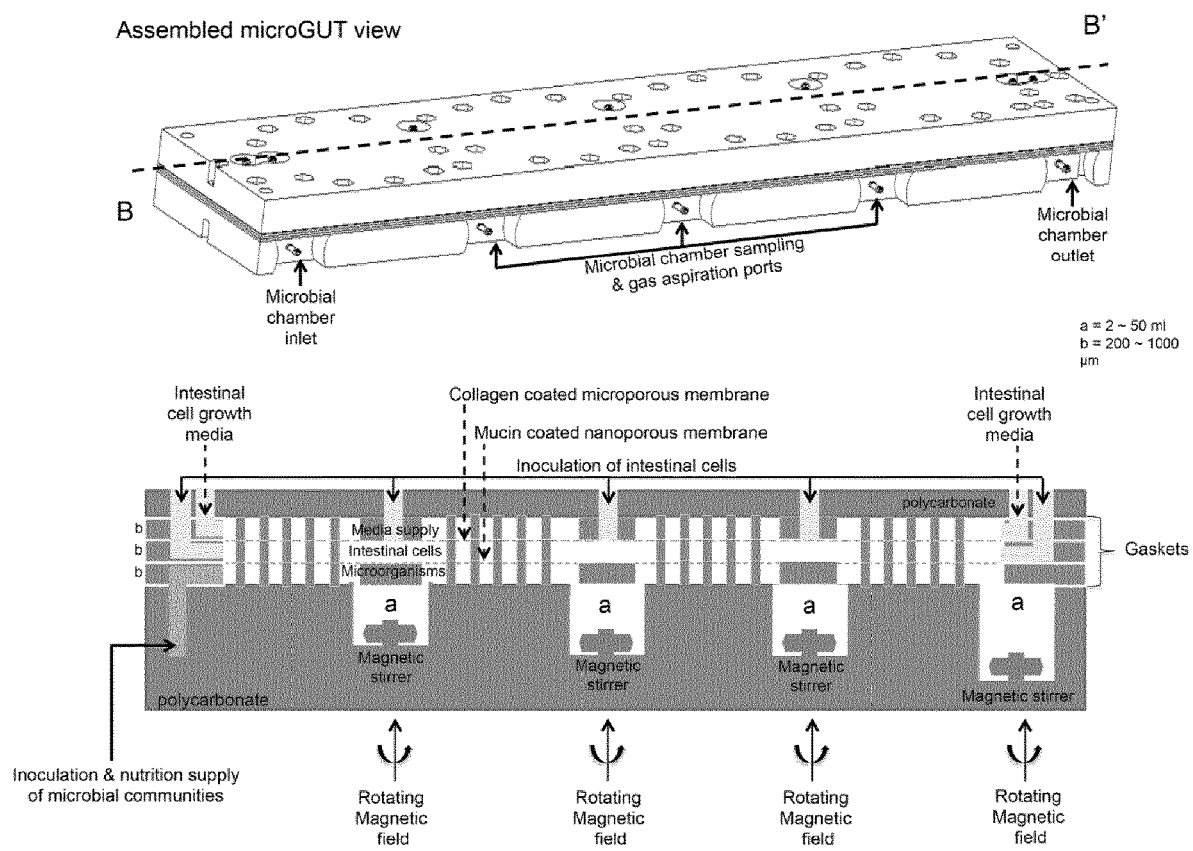
FIG. 3 shows apparatus of the invention together with a cross-section thereof.

FIG. 3 provides a cross-sectional view of the apparatus shown exploded in FIG. 2, and shows the charging point for the inoculum (arrow to bottom left), and rotating magnetic fields located beneath the magnetic stirrers. The vertical members depicted are gaskets separating the membranes, and the thin members are the walls of the double spiral shown in FIG. 1.

Figure 4:
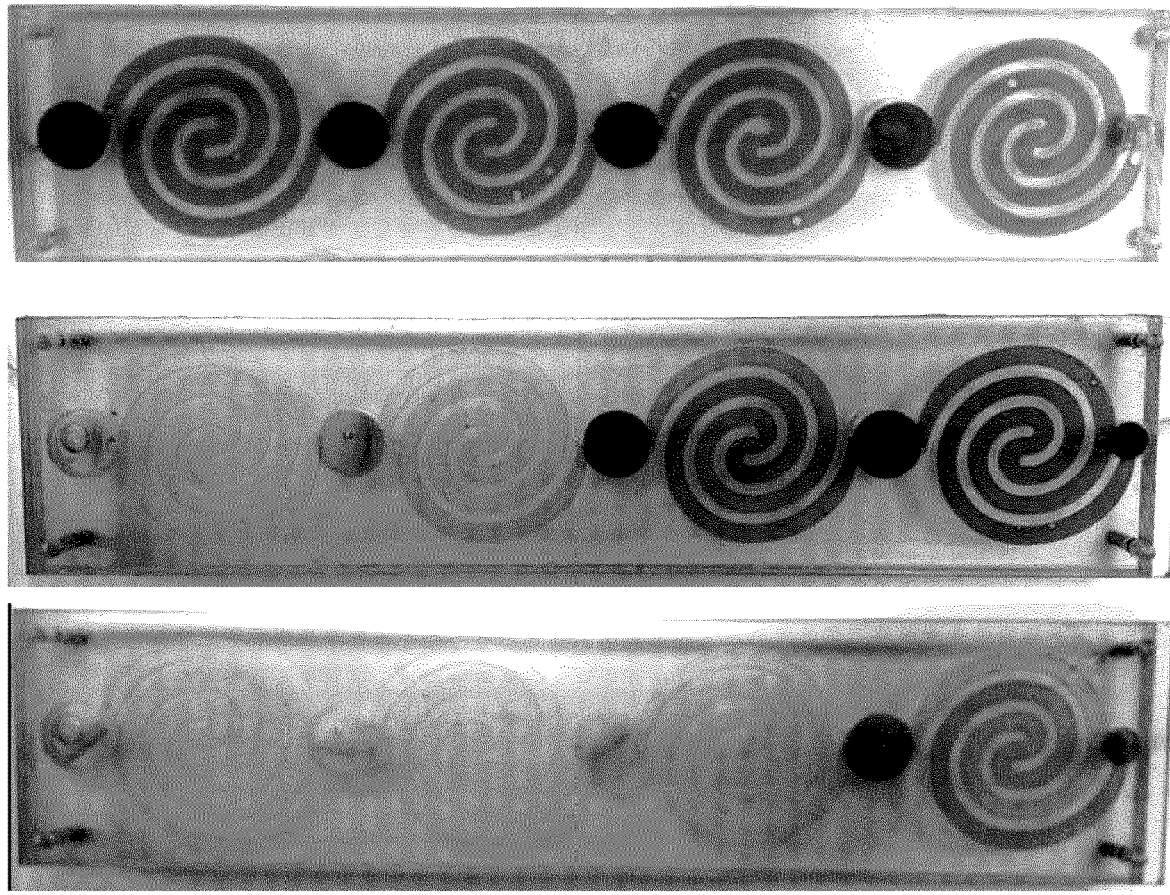
FIG. 4 shows how dye is flushed from the apparatus of the invention.
Figure 5:
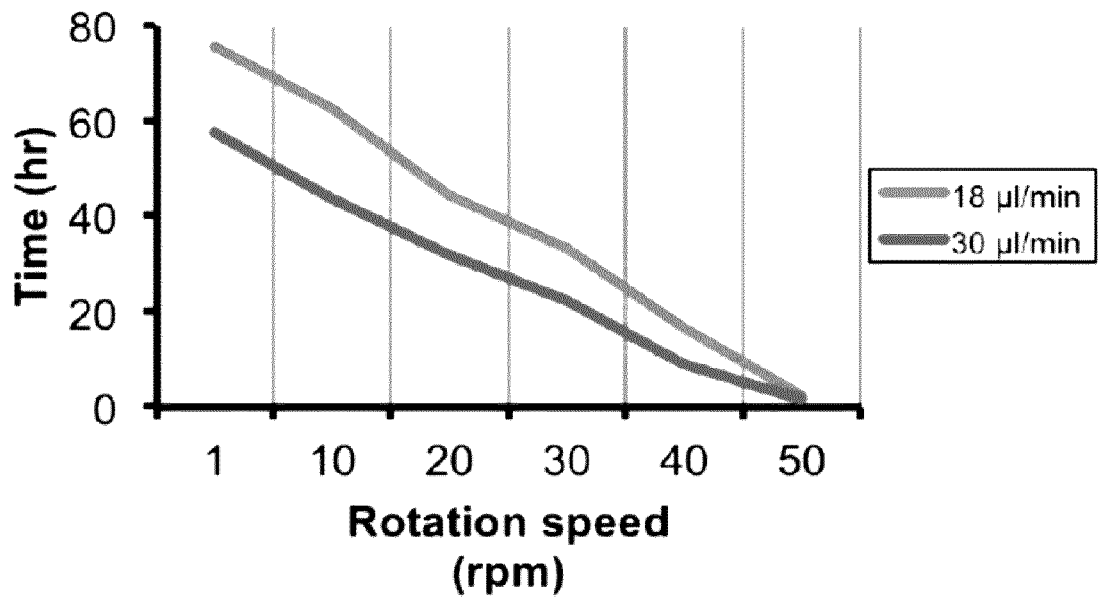
FIG. 5 is a graph of retention time plotted against flea rotation speed.

FIGS. 4 and 5 are described in detail in the following Examples.

The present invention will now be further illustrated by the following, non-limiting Examples.

EXAMPLES

Example 1

Residence Times:

We conducted an extensive investigation of the flow rates and residence times based on the rotational speeds of the magnetic stirrer bars. The model was designed to evaluate and demonstrate the possibility of controlling the individual residence times based on the tuning of the rotation speeds of the magnetic stirrer bars (FIG. 3). In order to characterise the retention times with respect to the rotational speeds, initially the flow rates were kept in the range of 18-30 µl/min (typical flow rates optimised for biomimetic cultures) and the rotation speeds were then changed from 1-50 rpm (in increments of 10) to characterise the residence times.

In order to ascertain the retention time, a dyed solution was loaded in the microGUT model and, subsequently, the model was perfused with plain dye-less water. The time required to completely eradicate the dye solution from the various sections of the microGUT model provide the retention time at that particular flow rate and rotation speed (FIG. 4). Our results highlighted a fairly linear relationship between the rotation speeds (i.e. mixing or dilution rate of the reactors with the newly flushed medium) and retention time of the fluid (FIG. 5). The programmable range of the retention times were between about 2-76 hours, which is sufficient to mimic the typical fluid retention times of the human gastrointestinal tract ranging from about 12 to about 76 hours.

Example 2

Co-Culture Feasibility Study

We designed a feasibility study to ascertain the possibility of culturing a complex faecal microbiota in the microGUT model. It was known that it was possible to co-culture human and microbial cells. In this experiment, we sought to confirm that it was possible to sustain a culture of complex faecal microflora in microGUT model up to 10 days. For this, we used a version of the microGUT model with only the microbial, or luminal, compartment, and containing only a single channel for adherent mucosal microbiota interlaced with bioreactors for luminal microbiota. A magnetic stirrer plate was used for actuation of magnetic stirrer bars sealed inside the bioreactors. This model was used to evaluate if complex fecal microbiota can be cultured in the microGUT model (FIG. 5). A complex microbial community prepared by pooling three fecal samples from healthy donors was inoculated in the microGUT model. Flow rates were as Example 1, and a peristaltic pump was used to drive the flow.

For the first 3 days, the inoculate was fed with a complex microbial medium designed for supporting the growth of diverse gastrointestinal microbiota (25). After 3 days of this equilibration phase, which results in homogeneous growth of the microbial community across the various sections of the microGUT model, we sampled the luminal bioreactors to ascertain the composition of their microbial communities. For the next 10 days, the microGUT model was perfused with gastrointestinal enzymes (bile, and pancreatic acids) twice a day, simulating human feeding patterns. Intermittent samples were taken from the luminal reactors for pH measurement. Over the course of the experiment, a pH gradient was created across the microGUT model starting from acidic conditions in the stomach, through to the pH neutral distal colon. Volatile gases were removed from the luminal bioreactors, using an aeration needle connected to a three-port manual valve.

After 10 days of culture of the fecal inocula, the microGUT model was disassembled and the final community samples were determined from the mucosal and luminal reactors. DNA extracts from the community samples of the inocula, equilibrated community (3 days), as well as the final community (after 10 days of feeding regime), were subjected to 16S rRNA amplicon sequencing.

Below are presented the results of a 2-week culture of sampled fecal microbiota containing over 600 individual bacteria in the microGUT model. After 2 weeks, we characterised the cultured community via 16S rRNA profiling and discovered the presence of up to 590 bacteria in the final stabilised community. The first round of high-throughput omic analyses confirms that the microGUT model permits the culture of complex microbial communities of the sampled fecal microbiota (Table 1).

Table 1: 16S rRNA amplicon sequencing of the microGUT samples. Results of the proof of concept experiments demonstrate the ability of the microGUT model to sustain complex, sampled human fecal inocula in a microGUT model for up to 2 weeks. The high Shannon species diversity indicates that a few species were more abundant than the overall community members, which was the result of the overgrowth of certain members of Proteobacteria (n=2).

| Sample | Shannon species diversity | No. of species identified |
| --- | --- | --- |
| Fecal inoculate | 2.795 | 635 |
| Average equilibriated communities after 3 day culture (n = 2) | | |
| Ascending colon | 2.529 | 530 |
| Transverse colon | 2.411 | 558 |
| Descending colon | 2.422 | 565 |
| Average no. of species in the microGUT sections after 10 days of feeding regime (n = 2) | | |
| Small intestine mucosa | | 560.5 |
| Small intestine lumen | | 540.5 |
| Ascending colon mucosa | | 561.5 |
| Ascending colon lumen | | 598.5 |
| Transverse colon mucosa | | 558 |
| Transverse colon lumen | | 565 |
| Descending colon mucosa | | 596 |
| Descending colon lumen | | 560 |

Out of 635 species inoculated in the pooled fecal inoculate, up to 598 species survived in the various niches of the microGUT model. On average, the small intestinal sections had slightly less species diversity compared to the subsequent segments, which may be due to the acidic conditions in the small intestinal section.

This experiment was conducted without individualised regulation of the bioreactor stirrers, but using a single magnetic stirrer plate, so that the rotational speed of all the magnetic stirrer bars was the same. The retention time over the entire apparatus was controlled at 24 h, and so the retention time across each chamber was similar (~6 h), which is considered to have played a role in the settlement of similar numbers of species in the three subsequent colon segments.

Example 3

Automation:

After the positive outcomes of the above Experiments, a full-scale automated microGUT model was assembled. The modular assembly setup used elastomeric gaskets. These were prepared by laser cutting rubber sheets coated with laser-cut medical grade adhesive tape, thereby permitting attachment of scaffolding membranes anchoring and partitioning human and microbial cells.

The model was provided with integral sensors and sampling ports to allow for continuous monitoring of physicochemical parameters. An automated platform for controlling the actuation/rotation of the individual stirrer bars was provided. The platform consisted of stepper motors mounted on a stage underneath the microGUT mounting plate. Each stepper motor is mounted with a magnet which, when rotated, induces a similar rotation on the magnetic stirrer bar housed inside the luminal bioreactors mounted above the stepper motor. These stepper motors can be programmed to rotate at different speeds and thus induce a different retention time of the fluids in the various luminal bioreactors. Speeds were adjusted to provide individual retention times of the various sections of the model analogous to human gastrointestinal conditions.

REFERENCES

1. Flint, H. J., Scott, K. P., Louis, P., et al. (2012) The role of the gut microbiota in nutrition and health. *Nat Rev Gastroenterol Hepatol* 9, 577-89.

2. Pflughoeft, K. J. and Versalovic, J. (2011) Human Microbiome in Health and Disease. *Annu Rev Pathol*.

3. Fritz, J. V, Desai, M. S., Shah, P., et al. (2013) From meta-omics to causality: experimental models for human microbiome research. *Microbiome* 1, 14.

4. Wichmann, A., Allahyar, A., Greiner, T. U., et al. (2013) Microbial modulation of energy availability in the colon regulates intestinal transit. *Cell Host Microbe* 14, 582-90.

5. Rodes, L., Paul, A., Coussa-Charley, M., et al. (2011) Transit time affects the community stability of *Lactobacillus* and *Bifidobacterium* species in an in vitro model of human colonic microbiotia. *Artif Cells Blood Substit Immobil Biotechnol* 39, 351-6.

6. Kashyap, P. C., Marcobal, A., Ursell, L. K., et al. (2013) Complex interactions among diet, gastrointestinal transit, and gut microbiota in humanized mice. *Gastroenterology* 144, 967-77.

7. Molly, K., Woestyne, M., and Verstraete, W. (1993) Development of a 5-step multi-chamber reactor as a simulation of the human intestinal microbial ecosystem. *Appl Microbiol Biotechnol* 39, 254-258.

8. Lesuffleur, T., Barbat, A., Dussaulx, E., et al. (1990) Growth Adaptation to Methotrexate of HT-29 Human Colon Carcinoma Cells Is Associated with Their Ability to Differentiate into Columnar Absorptive and Mucus-secreting Cells. *Cancer Res* 50, 6334-6343.

9. Coconnier, M.H., Klaenhammer, T.R., Kerneis, S., et al. (1992) Protein-mediated adhesion of *Lactobacillus acidophilus* BG2FO4 on human enterocyte and mucus-secreting cell lines in culture. *Appl Environ Microbiol* 58, 2034-2039.

10. Vesterlund, S., Karp, M., Salminen, S., et al. (2006) *Staphylococcus aureus* adheres to human intestinal mucus but can be displaced by certain lactic acid bacteria. *Microbiology* 152, 1819-1826.

11. Macfarlane, S., Woodmansey, E. J., and Macfarlane, G.T. (2005) Colonization of Mucin by Human Intestinal Bacteria and Establishment of Biofilm Communities in a Two-Stage Continuous Culture System. *Appl Environ Microbiol* 71, 7483-7492.

12. Shen, H., Hu, Y., and Saltzman, W. M. (2006) DNA Diffusion in Mucus: Effect of Size, Topology of DNAs, and Transfection Reagents. *Biophys J* 91, 639-644.

13. Estes, M. D., Ouyang, B., Ho, S., et al. (2009) Isolation of prostate cancer cell subpopulations of functional interest by use of an on-chip magnetic bead-based cell separator. *J. Micromechanics Microengineering* 19, 95015.

14. Hopwood, A. J., Hurth, C., Yang, J., et al. (2010) Integrated microfluidic system for rapid forensic DNA analysis: sample collection to DNA profile. *Anal Chem* 82, 6991-6999.

15. Hidalgo, I, J., Raub, et al. (1989) Characterization of the human colon carcinoma cell line (Caco-2) as a model system for intestinal epithelial permeability. *Wiley, Hoboken*, NJ, ETATS-UNIS.

16. Gibson, G. R., Cummings, J. H., and Macfarlane, G. T. (1988) Use of a three-stage continuous culture system to study the effect of mucin on dissimilatory sulfate reduction and methanogenesis by mixed populations of human gut bacteria. *Appl Environ Microbiol* 54, 2750-2755.

17. Nuenen, M. H. M. C. van, Diederick Meyer, P., and Venema, K. (2003) The Effect of Various Inulins and Clostridium difficile on the Metabolic Activity of the Human Colonic Microbiota in vitro. *Microb Ecol Health Dis* 15, 137-144.

18. Abbeele, P. Van den, Grootaert, C., Marzorati, M., et al. (2010) Microbial Community Development in a Dynamic Gut Model Is Reproducible, Colon Region Specific, and Selective for Bacteroidetes and Clostridium Cluster IX. *Appl Environ Microbiol* 76, 5237-5246.

19. Skolimowski, M., Nielsen, M. W., Emnéus, J., et al. (2010) Microfluidic dissolved oxygen gradient generator biochip as a useful tool in bacterial biofilm studies. *Lab Chip* 10, 2162-9.

20. Shah, P., Vedarethinam, I., Kwasny, D., et al. (2011) Microfluidic bioreactors for culture of non-adherent cells. *Sensors Actuators B Chem* 156, 1002-1008.

21. Yamashita, S., Konishi, K., Yamazaki, Y., et al. (2002) New and better protocols for a short-term Caco-2 cell culture system. *J. Pharm Sci* 91, 669-79.

22. Barranco, S. C., Townsend, C. M., Casartelli, C., et al. (1983) Establishment and Characterization of an in Vitro Model System for Human Adenocarcinoma of the Stomach. *Cancer Res* 43, 1703-1709.

23. Sekiguchi, M., Sakakibara, K., and Fujii, G. (1978) Establishment of cultured cell lines derived from a human gastric carcinoma. *Jpn J Exp Med* 48, 61-68.

24. Romano, M, Razandi, et al. (1988) Human cell line for study of damage to gastric epithelial cells in vitro. *J Lab Clin Med* 111, 430-440.

25. Goodman, A., Kallstrom, G., and Faith, J. (2011) Extensive personal human gut microbiota culture collections characterized and manipulated in gnotobiotic mice. *Proc.*

The invention claimed is:

1. A cell culture apparatus for emulating gastrointestinal tract conditions, comprising:
   a first layer, a set of first channels formed in the first layer, the set of first channels configured to support culture of gastrointestinal tract epithelial cells by providing laminar flow therein;
   a second layer, a set of second channels formed in the second layer, the set of second channels configured to support culture of luminal microbiota and mucosal cells by providing laminar flow therein;
   a set of dwell chambers, each of the set of dwell chambers in fluid communication with a corresponding second channel and structured to provide a location for unattached luminal microbiota to reside away from any direct flow in the second channel;
   an agitation mechanism disposed in each of the set of dwell chambers, the agitation mechanism comprising at least one of an impeller, a magnetic flea, rotary fins, or a stirring rod, the agitation mechanism configured to stir the media so as to promote growth of the unattached luminal flora within the dwell chamber; and
   a first membrane positioned between the each of the set of first channels and a corresponding second channel of the set of second channels, the first membrane comprising at least one of a permeable or semi-permeable membrane configured to prevent passage of cells thereacross.

2. The cell culture apparatus of claim 1, wherein each of the set of first channel and the set of second channels have a cross-section, at least one dimension of the cross-section being less than 1 mm.

3. The cell culture apparatus of claim 1, wherein each of the set of first channels and the set of second channels comprise at least one entrance port and at least one exit port to permit passage of gastrointestinal tract epithelial cells and luminal microbiota therethrough, respectively.

4. The cell culture apparatus of claim 1, wherein each of the set of first channels are fluidly coupled to each other.

5. The cell culture apparatus of claim 1, further comprising:
   a third layer positioned on the first layer opposite the second layer, a set of third channels formed in the third layer corresponding to the set of first channels and configured to allow passage of nutrient media therethrough; and
   a second membrane positioned between each of the set of first channels and the set of third channels, the second membrane comprising at least one of a permeable or semi-permeable membrane configured to prevent passage of cells thereacross.

6. The cell culture apparatus of claim 5, wherein the first membrane comprises a mucin coated nanoporous membrane, and wherein the second membrane comprises a collagen coated microporous membrane.

7. The cell culture apparatus of claim 1, wherein:
   said second channel is formed in a bottom layer,
   the cell culture apparatus further comprises a bottom plate disposed below the bottom layer, the set of dwell chambers formed in the bottom plate, and
   ports are defined through the bottom plate to at least a portion of the set of dwell chambers for gas aspiration and drawing microbial samples from at least the portion of set of dwell chambers during operation.

8. A cell culture apparatus for emulating gastrointestinal tract conditions, comprising:
   at least two adjacent cell cultivation channels separated by a permeable or semipermeable membrane adapted to prevent passage of cells thereacross, at least two of said channels having a cross section for the majority of the length of said channel having two dimensions, and wherein at least one dimension of each of said cross sections does not exceed 1000 μm such that the channels provides laminar flow, each said channel being provided with at least one entrance port and at least one exit port to permit the passage of media through at least a portion of the channel having a cross sectional area of no more than 10 mm$^2$, a first channel of said at least two channels being adaptable to support the culture of gastrointestinal tract epithelial cells and a second channel of said at least two channels being adaptable to support luminal mucosal cells and microbiota such that the gastrointestinal tract epithelial cells and the luminal mucosal cells adhere in their respective channels due to laminar flow therein, and wherein said second channel comprises one or more dwell chambers capable of providing a location for unattached luminal flora to reside away from any direct flow in said second channel,
   wherein each of the dwell chambers comprises an agitation mechanism comprising at least one of an impeller, a magnetic flea, rotary fins, or a stirring rod disposed in the dwell chamber, the agitation mechanism configured to stir the media so as to promote growth of the unattached luminal flora within the dwell chamber.

9. The cell culture apparatus according to claim 8, wherein the at least two cell cultivation channels are made of at least one of plastic, polycarbonate, polystyrene, silicone.

10. The cell culture apparatus according to claim 8, wherein said apparatus is constructed in layers, with individual layers for each channel and for each membrane.

11. The cell culture apparatus according to claim 10, wherein the adjacent cell cultivation channels take the form of a paired helix.

12. The cell culture apparatus according to claim 8, further comprising a third channel, the third channel separated from said first channel by a semipermeable membrane, the third channel configured to carry nutrients for any cells in said first channel.

13. The cell culture apparatus according to claim 8, wherein said dwell chambers have volumes in a range of 0.5-50 ml, said volumes configured to set a retention time of the luminal microbiota in the dwell chambers.

14. The cell culture apparatus according to claim 8, wherein each dwell chamber is configured to demarcate an emulated section of gut.

15. The cell culture apparatus according to claim 12, further comprising one or more biosensors.

16. The cell culture apparatus according to claim 15, wherein said one or more biosensors are for monitoring at least one of a quality and state of the system.

17. The cell culture apparatus of claim 8, wherein:
   said second channel is formed in a bottom layer,
   the cell culture apparatus further comprises a bottom plate disposed below the bottom layer, the one or more dwell chambers formed in the bottom plate and fluidly coupled to each other via the second channel, and
   ports are defined through the bottom plate to at least a portion of the one or more dwell chambers for gas aspiration and drawing microbial samples from at least the portion of the one or more dwell chambers during operation.

* * * * *